United States Patent [19]

Schirmer

[11] 4,328,165
[45] May 4, 1982

[54] PENYLCARBAMIC ACID CHLORIDES AND THEIR PREPARATION

[75] Inventor: Ulrich Schirmer, Heidelberg, Fed. Rep. of Germany

[73] Assignee: BASF Aktiengesellschaft, Fed. Rep. of Germany

[21] Appl. No.: 120,939

[22] Filed: Feb. 12, 1980

[30] Foreign Application Priority Data

Mar. 8, 1979 [DE] Fed. Rep. of Germany ....... 2909198

[51] Int. Cl.³ .................... C07C 83/10; C07C 155/02; C07C 125/06; C07C 121/52
[52] U.S. Cl. ................... 260/453 RW; 260/455 A; 260/453 P; 260/465 D; 560/30; 560/31; 560/29; 564/53
[58] Field of Search ....... 260/455 A, 453 RW, 453 P, 260/465 D; 560/30, 31, 29; 564/53

[56] References Cited

U.S. PATENT DOCUMENTS

| | | | |
|---|---|---|---|
| 2,983,747 | 5/1961 | Campbell et al. | 260/455 A |
| 3,867,426 | 2/1975 | Olin et al. | 560/32 |
| 3,884,951 | 5/1975 | Oswald | 260/455 A |
| 4,013,450 | 3/1977 | Olin et al. | 71/111 |

FOREIGN PATENT DOCUMENTS 873084  6/1974  Fed. Rep. of Germany ... 260/455 A

OTHER PUBLICATIONS

Noller, Textbook of Organic Chemistry, 2nd Edition, W. B. Saunders Co., Philadelphia, 1958.
Houben–Weyl, Methoden der Organischen Chemie, vol. 8 (1952), pp. 115–124.
Chem. Berichte, 19 (1886), pp. 546–551.
Reid, Organic Chemistry of Bivalent Sulfur, Chemical Publishing Co., Inc., N. Y., 1958, p. 108.

Primary Examiner—Henry R. Jiles
Assistant Examiner—Robert C. Whittenbaugh
Attorney, Agent, or Firm—Keil & Witherspoon

[57] ABSTRACT

Novel phenylcarbamic acid chlorides, and their preparation by reacting N-mono-substituted phenylenediamines with excess phosgene and then reacting the products with thioalcohols, alcohols, hydroxylamines or amines.

The novel phenylcarbamic acid chlorides of the formula I obtainable by the process of the invention are valuable intermediates for the preparation of crop protection agents, especially herbicides.

7 Claims, No Drawings

PHENYLCARBAMIC ACID CHLORIDES AND THEIR PREPARATION

The present invention relates to novel phenylcarbamic acid chlorides and to their preparation by reacting N-monosubstituted phenylenediamines with excess phosgene and then reacting the products with thioalcohols, alcohols, hydroxylamines or amines.

Houben-Weyl, Methoden der Organischen Chemie, Volume 8, pages 115-124, and Ann. Chem. 562 (1949), 75-136 disclose the reaction of aromatic amines with phosgene to give phenyl isocyanates; adduct formation with hydrogen chloride, for example from the off-gas of the reaction, results in the corresponding phenylcarbamic acid chlorides. In the case of diamines, the corresponding diisocyanates are formed. No information is given on diamines in which the two amino groups behave differently in the reaction. According to a disclosure in Ann. Chem. (loc. cit., page 84) isocyanatocarbamic acid chlorides can only be obtained on phosgenating the hydrochlorides of aliphatic primary-secondary amines; only the preparation of hexylisocyanato-N-butylcarbamic acid chloride is described.

Angew. Chem., 74 (1962), 795-799 discloses that the treatment of toluylene-2,4-diisocyanate with equimolar amounts of hydrochloric acid results in the corresponding p-methyl-m-isocyanato-carbamic acid chloride.

German Pat. No. 873,084 discloses that the phosgenation of diamines, containing a primary amino group and a secondary amino group, at elevated temperatures gives isocyanatocarbamic acid chlorides. Only the preparation of N-butyl-N-(ω-isocyanatohexyl)-carbamic acid chloride and of the corresponding N-(α-ethylhexyl)-N-(ω-isocyanatohexyl)-carbamic acid chloride are described. The same Patent points out that such carbamic acid chloride isocyanates are converted to diurethanes merely on dissolved in ethyl alcohol.

I have found that phenylcarbamic acid chlorides of the formula I

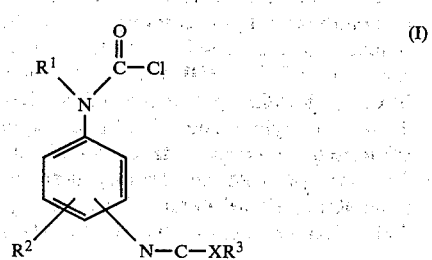
(I)

where X is oxygen, sulfur or

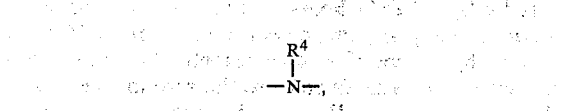

$R^1$ is an aliphatic radical, $R^2$, $R^3$ and $R^4$ are identical or different and are each an aliphatic, cycloaliphatic, araliphatic or aromatic radical, $R^4$ can also be hydrogen or alkoxy and $R^2$ can also be hydrogen, halogen, nitro or alkoxy, are obtained in an advantageous manner if an N-monosubstituted phenylenediamine of the formula II

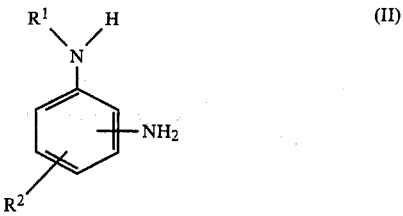
(II)

where $R^1$ and $R^2$ have the above meanings, is reacted, in a first step, with an excess of phosgene at from $-30°$ C. to $+200°$ C. and the resulting isocyanatophenylcarbamic acid chloride of the formula III

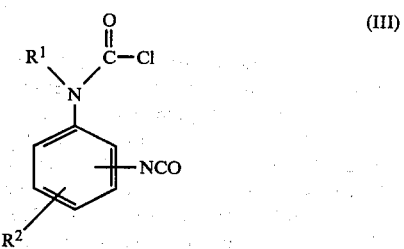
(III)

where $R^1$ and $R^2$ have the above meanings, is reacted in a second step, without prior isolation, with a compound of the formula IV $$H-X-R^3 \qquad (IV)$$

where $R^3$ and X have the above meanings.

Further, I have found the novel phenylcarbamic acid chlorides of the formula I

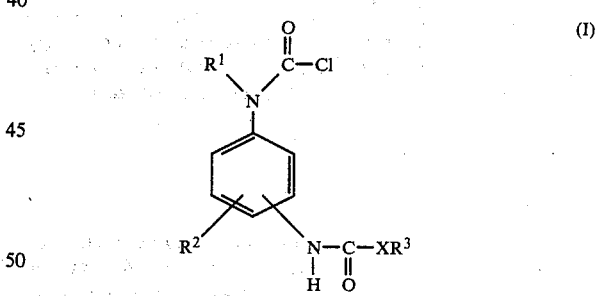
(I)

where X is oxygen, sulfur or

$R^1$ is an aliphatic radical, $R^2$, $R^3$ and $R^4$ are identical or different and are each an aliphatic, cycloaliphatic, araliphatic or aromatic radical, $R^4$ can also be hydrogen or alkoxy and $R^2$ can also be hydrogen, halogen, nitro or alkoxy.

If N-methyl-m-phenylenediamine and methanol are used, the reaction can be represented by the following equations:

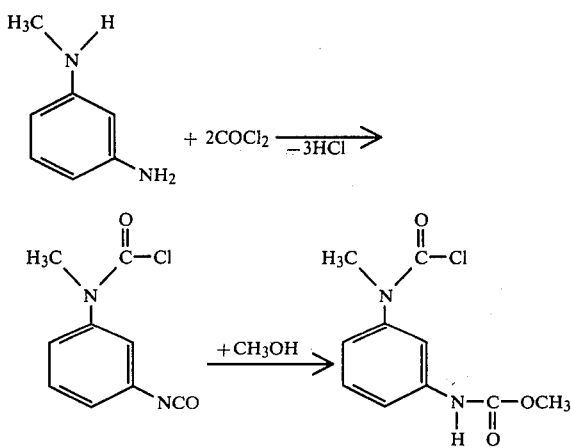

The invention is based on the observation that a one-vessel reaction of the mixture formed on preparation of an isocyanatophenylcarbamic acid chloride III, with a compound of the formula IV, gives a phenylcarbamic acid chloride I in a surprisingly advantageous manner. Compared to the prior art, the novel process gives a large number of the novel phenylcarbamic acid chlorides in a simple and economical manner, in good yield and high purity. All these advantageous results of the process according to the invention are surprising since it would have been expected, taking into account the above publications, that particularly in the case of an aromatic diamine a reaction of both amino groups, to give a diurethane, would occur and that because of the one-vessel method used, without intermediate isolation of the compound III, a heterogeneous mixture of numerous by-products would form.

The starting materials II can be prepared easily by conventional processes, for example by the process described in Berichte, 19 (1886), 546–551. Phosgene is employed in excess, preferably in an amount of from 2.1 to 8, especially 2.1 to 4, moles per mole of starting material II. Preferred starting materials II and accordingly preferred compounds III and IV and preferred end products I are those where X is oxygen, sulfur or

$R^1$ is alkyl of 1 to 7 carbon atoms or alkenyl or alkynyl, each of 2 to 7 carbon atoms, $R^2$, $R^3$ and $R^4$ may be identical or different and each is alkyl or chloroalkyl of 1 to 7 carbon atoms, cyanoalkyl, alkenyl or alkynyl each of 2 to 7 carbon atoms, monocyclic or bicyclic cycloalkyl of 5 to 10 carbon atoms, aralkyl or alkylaryl, each of 7 to 12 carbon atoms, or phenyl which is unsubstituted or substituted by halogen, especially fluorine or chlorine, $R^4$ may also be hydrogen or alkoxy of 1 to 4 carbon atoms, and $R^2$ may also be hydrogen, bromine or in particular chlorine, nitro or alkoxy of 1 to 7 carbon atoms. The two nitrogen atoms of the starting compound II may be in the o-position or advantageously in the p-position or, preferably, in the m-position. The above radicals may in addition be substituted by groups or atoms which are inert under the reaction conditions, eg. alkyl or alkoxy each of 1 to 4 carbon atoms or by fluorine or chlorine present on an aromatic nucleus.

Examples of suitable starting materials II are N-methyl-, N-ethyl-, N-propyl-, N-isopropyl-, N-butyl-, N-isobutyl-, N-sec.-butyl-, N-tert.-butyl-, N-allyl- and N-propargyl-1,2-phenylenediamine and the corresponding 1,4-phenylenediamines and, preferably, 1,3-phenylenediamines, as well as homologous phenylenediamines which are substituted in the 2-,3-,4-, 5- or, in particular, 6-position by bromine, chlorine, nitro, methoxy, ethoxy, propoxy, isopropoxy, butoxy, isobutoxy, sec.-butoxy, tert.-butoxy, methyl, ethyl, propyl, isopropyl, butyl, isobutyl, sec.-butyl, tert.-butyl, allyl, crotyl, propargyl, cyclopentyl, cyclohexyl, benzyl, tolyl or phenyl.

The first step of the reaction is carried out at from $-30°$ C. to $+200°$ C., preferably from $-15°$ to $+140°$ C., under atmospheric or superatmospheric pressure, continuously or batchwise. Advantageously, a solvent which is inert under the reaction conditions is used. Examples of suitable solvents are aromatic hydrocarbons, eg. toluene, ethylbenzene, o-, m- and p-xylene, isopropylbenzene and methylnaphthalene; halohydrocarbons, especially chlorohydrocarbons, eg. tetrachloroethylene, 1,1,2,2- or 1,1,1,2-tetrachloroethane, chloroform, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, chlorobenzene, fluorobenzene, bromobenzene, iodobenzene, o-, p- and m-dichlorobenzene, o-, m- and p-chlorotoluene, 1,2,4-trichlorobenzene, 1,10-dibromodecane and 1,4-dibromobutane; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane and thioanisole; ketones, eg. methyl ethyl ketone, acetone, diisopropyl ketone, diethyl ketone, methyl isobutyl ketone, mesityl oxide, acetophenone, cyclohexanone, ethyl isoamyl ketone, diisobutyl ketone, methylcyclohexanone and dimethylcyclohexanone; nitrohydrocarbons, eg. nitromethane, nitroethane, nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, α-pinene, pinane, nonane, gasoline fractions boiling within the range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; and mixtures of the above. The solvent is advantageously used in an amount of from 400 to 10,000 percent by weight, preferably from 700 to 1,800 percent by weight, based on starting material II.

The first step of the reaction may be carried out as follows: a mixture of starting material II and phosgene, with or without solvent, is kept at the reaction temperature for from 1 to 24 hours. In a preferred embodiment, a part of the phosgene, advantageously from 25 to 75 percent by weight of the total amount of phosgene, and the solvent are introduced into the reaction vessel and the starting material II is added slowly, for example in the course of from 0.5 to 4 hours, advantageously at from $-20°$ to $+10°$ C.; the remaining phosgene is then introduced; advantageously in the course of from 1 to 10 hours, and advantageously whilst heating the mixture at from 80° to 150° C. Thereafter the reaction mixture—advantageously after removal of excess phosgene by means of nitrogen—is subjected to the second step of the reaction. If desired, a part of the solvent, advantageously from 10 to 80 percent by weight of the total amount of solvent, can also be removed from the reaction mixture, for example by fractional distillation, before starting the second step.

The reaction mixture resulting from the first step is reacted in the second step with an alcohol, thioalcohol, N- or O-substituted hydroxylamine or amine of the formula IV used in the stoichiometric amount or in excess, preferably with from 1 to 2 moles of compound IV per mole of starting material II.

Examples of suitable starting materials IV are methyl, ethyl, propyl, isopropyl, butyl, isobutyl, sec.-butyl, tert.-butyl, allyl, crotyl, propargyl, cyclopentyl, cyclohexyl, benzyl, 1,1-dimethylpropargyl and cyanomethyl alcohol, phenol, o-methylphenol, m-methylphenol and p-methylphenol, the corresponding thioalcohols, amines which are monosubstituted or disubstituted at the nitrogen by the above substituents, which may be identical or different in the case of disubstitution, and corresponding N-monosubstituted and N,O-disubstituted hydroxylamines. The reaction is in general carried out at from $-10°$ C. to $+100°$ C., preferably from $-5°$ C. to $+30°$ C., under atmospheric or superatmospheric pressure, continuously or batchwise. Advantageously, a solvent which is inert under the reaction conditions is used. In general terms, suitable solvents are the same as those mentioned for the first step of the reaction.

The second step of the reaction may be carried out as follows: the mixture from the first reaction step, which contains compound III, is kept, together with starting material IV, and with or without additional solvent, at the reaction temperature for from 0.5 to 6 hours. The end product is then isolated from the reaction mixture in a conventional manner, for example by filtration.

The novel phenylcarbamic acid chlorides of the formula I obtainable by the process of the invention are valuable intermediates for the preparation of crop protection agents. For example, they may be reacted with alcohols, thiols or amines to give the corresponding dicarbamic acid esters, thioesters and diureas, which are valuable herbicides. For details, reference may be made, for example, to U.S. Pat. Nos. 3,867,426 and 4,013,450 and to German Laid-Open Applications DOS No. 2,703,838 and DOS No. 2,725,146.

In the Examples which follow, parts are by weight and bear the same relation to parts by volume as that of the kilogram to the liter.

EXAMPLE 1

80 parts of phosgene are introduced into 200 parts of toluene at from $-10°$ to $-15°$ C. 40 parts of N-methyl-m-phenylenediamine in 300 parts of toluene are then added in the course of 1½ hours at $-10°$ C., with efficient stirring. The batch is heated to 20° C. in the course of 2 hours, then to 60° C. in the course of one hour, and finally to 110° C. in the course of 2 hours, resulting in the formation of a clear solution, with vigorous evolution of gas. The mixture is then refluxed for 4 hours at 110° C., whilst introducing phosgene at the rate of 30 parts per hour. Thereafter, the mixture is concentrated to 200 parts by volume under reduced pressure, 18 parts of ethyl alcohol are added at 20° C., and after a reaction time of 24 hours at 20° C. the mixture is concentrated under reduced pressure. This results in a viscous oil which is caused to crystallize by adding a toluene/petroleum ether mixture. After filtering the mixture, washing the filter residue and drying it under reduced pressure, 80 parts (95% of theory) of O-ethyl-N-(3-(N'-methyl-N'-chlorocarbonyl)-aminophenyl)-carbamate, of melting point 63°–65° C., are obtained.

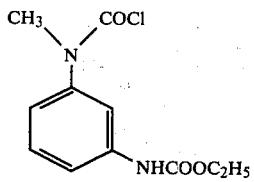

EXAMPLE 2

14.8 parts of dimethylamine in 150 parts of toluene are added, at 0° C., to a solution of N-(3-isocyanatophenyl)-N-methylcarbamic acid chloride which has been prepared, similarly to Example 1, from 40 parts of N-methyl-m-phenylenediamine and has been concentrated to 200 parts by volume. After stirring for two hours at 10° C., the mixture is filtered and the filter residue is washed with toluene and dried under reduced pressure. 69 parts (82% of theory) of N,N-dimethyl-N'-(3-(N''-methyl-N''-chlorocarbonyl)-aminophenyl)-urea of melting point 76°–77° C. are obtained.

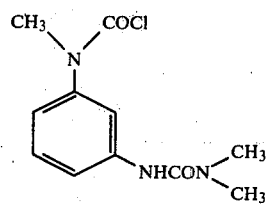

EXAMPLES 3 TO 20

The end products I shown in the Table are prepared by methods similar to the preceding Examples, merely varying the starting materials II and IV.

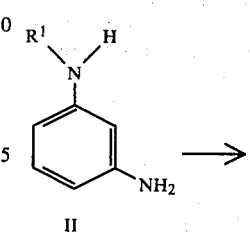

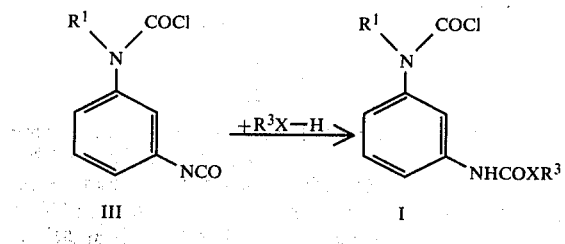

| Example | Starting material II R¹ = | Parts | Starting material IV R³X = | Parts | Method similar to Example | Yield of end product I in % of theory | Melting point, °C., of end product I |
|---|---|---|---|---|---|---|---|
| 3 | CH₃ | 40 | CH₃NH— | 10.2 | 2 | 90 | 157–159 |
| 4 | CH₃ | 40 | CH₃S— | 16.2 | 1 | 84 | 176–177 |
| 5 | CH₃ | 40 | (CH₃)₃C—O— | 29.8 | 1 | 42 | 119–121 |
| 6 | CH₃ | 40 | C₂H₅—S— | 29.4 | 1 | 87 | 97–99 |
| 7 | CH₃ | 40 | (CH₃)₂CHO— | 29.6 | 1 | 100 | very viscous oil |
| 8 | C₂H₅ | 44.5 | CH₃O— | 10.8 | 1 | 92 | 86–88 |
| 9 | C₂H₅ | 44.5 | CH₃S— | 16.2 | 1 | 84 | 104–106 |
| 10 | CH₃ | 40 | (CH₃)₃C—NH— | 22.6 | 2 | 90 | 178–180 |
| 11 | CH₃ | 40 | (CH₃)(CH₃O)N— | 20 | 2 | 54 | 91–93 |
| 12 | CH₃ | 40 | C₆H₅—O— | 30.8 | 1 | 100 | very viscous oil |
| 13 | CH₃ | 40 | C₆H₅—S— | 54.1 | 1 | 89 | 125–126 |
| 14 | CH₃ | 40 | Cl-C₆H₃(Cl)—S— | 71.2 | 1 | 64 | 107–108 |
| 15 | CH₃ | 40 | C₆H₅—CH₂O— | 40.8 | 1 | 64 | 89–91 |
| 16 | CH₃ | 40 | (cyclohexyl)—O— | 42.1 | 1 | 33 | 96–97 |
| 17 | CH₃ | 40 | (C₆H₅)(cyclohexyl)N— | 65.3 | 2 | 68 | 183–184 |
| 18 | CH₃ | 40 | F-C₆H₄—N(CH₂CN)— | 49.2 | 2 | 56 | 180–182 |
| 19 | CH₃ | 40 | Cl-C₆H₃(Cl)—CH₂NH— | 57.7 | 2 | 90 | 159–160 |
| 20 | CH₃ | 40 | CH₃O | 14.4 | 1 | 87 | 118–120 |

EXAMPLE 21 (USE)

5.5 parts of sodium 4-chlorophenolate in 100 parts of acetonitrile are added to 10 parts of S-methyl-N-(3'-[N'-methyl-N'-chlorocarbonyl]-aminophenyl)-thiolcarbamate from Example 4, in 200 parts of acetonitrile at 20° C. The temperature rises to 27° C., and after having been stirred for two hours the mixture is filtered and concentrated, and the residue is recrystallized from toluene. 5.3 parts of a white crystalline compound of melting point 149°–152° C. are obtained; the compound has the following structural formula

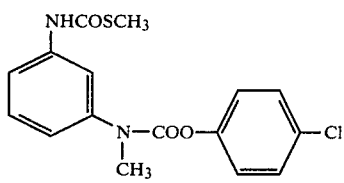

EXAMPLE 22 (USE)

5.75 parts of dimethylamine in 60 parts of toluene are added to 13.7 parts of O-methyl-N-(3'-[N'-methyl-N'-chlorocarbonyl]-aminophenyl)-carbamate from Example 20, suspended in 250 parts of toluene, at from 20° to 30° C.; the mixture is then stirred for 2 hours at 30° C., mixed with 100 parts of water and filtered. After drying the filter residue, 13.1 parts of a white, crystalline compound of melting point 166°–167° C. are obtained; the compound has the following structural formula

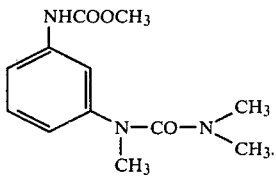

The following compounds are prepared by methods similar to Example 21 or Example 22.

| $R^5$ | $R^1$ | $R^6$ | Melting point in °C. |
|---|---|---|---|
| —OCH₃ | CH₃ | —O—C₆H₄—Cl | 183–185 |
| —S—C₆H₅ | CH₃ | —OCH₃ | 163–165 |
| —O—C(CH₃)₃ | CH₃ | —O—C₆H₅ | 134–136 |
| —O—C(CH₃)₃ | CH₃ | —N(CH₃)₂ | 145–147 |
| —OCH₃ | CH₃ | —NH—C₆H₅ | 170–172 |
| —OCH₃ | CH₃ | —N(CH₃)—C₆H₅ | 172–174 |
| —SCH₃ | CH₃ | —NH—C₆H₅ | 167–169 |
| —SCH₃ | CH₃ | —N(CH₃)—C₆H₅ | 123–125 |
| —OCH(CH₃)₂ | CH₃ | —N(CH₃)—C₆H₅ | 157–159 |
| —OC₂H₅ | CH₃ | —N(CH₃)₂ | 116–118 |
| —OCH₃ | CH₃ | —N(CH₃)—C₆H₄—CH₃ | 94–96 |
| —OCH₃ | CH₂CH₂Cl | —O—C₆H₅ | 141–143 |
| —OCH₃ | CH₃ | —O—C₆H₄—C₂H₅ | 98–100 |
| —OCH₃ | CH₃ | —O—C₆H₄—CH₃ | 130–132 |
| —SCH₃ | CH₃ | —O—C₆H₄—C₂H₅ | 123–126 |
| —NH—C(CH₃)₃ | CH₃ | —O—C₆H₅ | 186–188 |
| —OCH₃ | C₂H₅ | —O—C₆H₅ | 129–131 |

I claim:

1. A process for the preparation of a phenylcarbamic acid chloride of the formula I

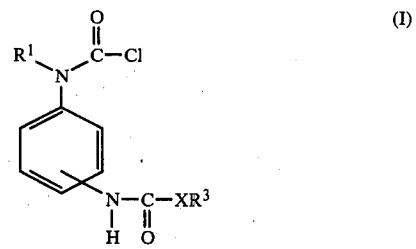

where X is oxygen or

$R^1$ is an alkyl or chloroalkyl each of 1 to 7 carbon atoms, $R^3$ and $R^4$ may be identical or different and each is alkyl or chloroalkyl of 1 to 7 carbon atoms, cyanoalkyl of 2 to 7 carbon atoms, cyclohexyl, benzyl or phenyl which is unsubstituted or substituted by fluorine or chlorine, $R^4$ may also be hydrogen or alkoxy of 1 to 4 carbon atoms, wherein an N-monosubstituted phenylenediamine of the formula II

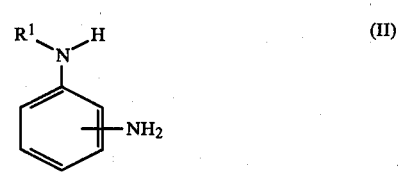

where $R^1$ has the above meanings, is reacted, in a first step, with an excess of phosgene at from −30° C. to +200° C. and the resulting isocyanatophenylcarbamic acid chloride of the formula III

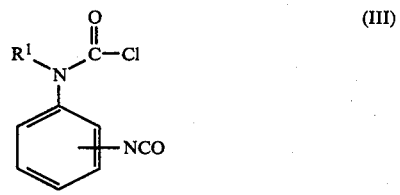

where $R^1$ has the above meanings, is reacted in the second step, without prior isolation, with a compound of the formula IV $$H—X—R^3 \qquad (IV)$$

where $R^3$ and X have the above meanings.

2. A phenylcarbamic acid chloride of the formula I

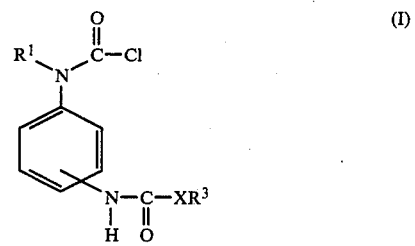

where X is oxygen or

$R^1$ is an alkyl or chloroalkyl each of 1 to 7 carbon atoms, $R^3$ and $R^4$ may be identical or different and each is alkyl or chloroalkyl of 1 to 7 carbon atoms, cyanoalkyl of 2 to 7 carbon atoms, cyclohexyl, benzyl or phenyl which is unsubstituted or substituted by fluorine or chlorine, $R^4$ may also be hydrogen or alkoxy of 1 to 4 carbon atoms.

3. The process of claim 1, wherein the reaction is carried out with from 2.1 to 8 moles of phosgene per mole of starting material II.

4. The process of claim 1, wherein the first step of the reaction is carried out at from −15° to +140° C.

5. The process of claim 1, wherein the reaction is carried out in the presence of a solvent which is inert under the reaction conditions.

6. The process of claim 1, wherein the reaction is carried out with from 1 to 2 moles of compound IV per mole of starting material II.

7. The process of claim 1, wherein the second step of the reaction is carried out at from −10° to +100° C.

* * * * *

UNITED STATES PATENT AND TRADEMARK OFFICE
CERTIFICATE OF CORRECTION

PATENT NO. : 4,328,165
DATED : May 4, 1982
INVENTOR(S) : Ulrich Schirmer

It is certified that error appears in the above—identified patent and that said Letters Patent is hereby corrected as shown below:

IN THE TITLE

In the title-Penylcarbamic should read Phenylcarbamic

Signed and Sealed this

Fourteenth Day of September 1982

[SEAL]

Attest:

GERALD J. MOSSINGHOFF

Attesting Officer        Commissioner of Patents and Trademarks